(12) United States Patent
Rasheed

(10) Patent No.: US 8,511,404 B2
(45) Date of Patent: *Aug. 20, 2013

(54) DRILLING TOOL, APPARATUS AND METHOD FOR UNDERREAMING AND SIMULTANEOUSLY MONITORING AND CONTROLLING WELLBORE DIAMETER

(76) Inventor: Wajid Rasheed, Slough (GB)

( * ) Notice: Subject to any disclaimer, the term of this patent is extended or adjusted under 35 U.S.C. 154(b) by 138 days.

This patent is subject to a terminal disclaimer.

(21) Appl. No.: 12/966,195

(22) Filed: Dec. 13, 2010

(65) Prior Publication Data

US 2012/0037422 A1   Feb. 16, 2012

Related U.S. Application Data

(63) Continuation-in-part of application No. PCT/ES2009/070261, filed on Jun. 27, 2009.

(30) Foreign Application Priority Data

Jun. 27, 2008 (GB) .................................. 0811815.0

(51) Int. Cl.
*E21B 10/00* (2006.01)
(52) U.S. Cl.
USPC ........................................ 175/384; 175/263
(58) Field of Classification Search
USPC ................. 175/385, 384, 390, 391, 334, 342, 175/263, 264–292

See application file for complete search history.

(56) References Cited

U.S. PATENT DOCUMENTS

| | | | |
|---|---|---|---|
| 4,665,511 A | 5/1987 | Rodney et al. | |
| 4,757,873 A | 7/1988 | Linyaev et al. | |
| 4,791,797 A | 12/1988 | Pake et al. | |
| 4,800,537 A | 1/1989 | Mount, II | |
| 4,802,145 A | 1/1989 | Mount, II | |
| 4,867,264 A | 9/1989 | Siegfried | |
| 4,916,400 A | 4/1990 | Best et al. | |
| 4,964,085 A | 10/1990 | Coope et al. | |
| 4,992,994 A | 2/1991 | Rambow et al. | |
| 5,130,950 A | 7/1992 | Orban et al. | |
| 5,175,429 A | 12/1992 | Hall, Jr. et al. | |
| 5,214,251 A | 5/1993 | Orban et al. | |
| 5,317,111 A | 5/1994 | Orban et al. | |
| 5,341,345 A | 8/1994 | Warner et al. | |
| 5,354,956 A | 10/1994 | Orban et al. | |
| 5,414,673 A | 5/1995 | Scherbatskoy | |
| RE34,975 E | 6/1995 | Orban et al. | |
| 5,459,697 A | 10/1995 | Chin et al. | |
| 5,469,736 A | 11/1995 | Moake | |
| 5,515,336 A | 5/1996 | Chin et al. | |
| 5,753,812 A | 5/1998 | Aron et al. | |
| 5,987,385 A | 11/1999 | Varsamis et al. | |
| 5,995,447 A | 11/1999 | Mandal et al. | |
| 6,002,639 A | 12/1999 | Birchak et al. | |

(Continued)

*Primary Examiner* — William P Neuder
*Assistant Examiner* — Kipp Wallace
(74) *Attorney, Agent, or Firm* — Fay Sharpe LLP

(57) ABSTRACT

The Smart Reamer® Tool, Apparatus or Method is used to underream an oil or natural gas well while interlinked calipers and calibration sensors simultaneously record data relating to the geometry of the drilling operation (well diameter, diameter of the underreamed zone) and drilling fluid properties (density). Further sensors provide data on the relative position of the cutting and stabilizing blocks. Other sensors measure vibration data. All the sensors are interlinked by means of microprocessors which compare and correlate said data to automatically verify and deliver a desired wellbore diameter without the need to unnecessarily stop drilling or trip out of the hole.

32 Claims, 9 Drawing Sheets

(56) References Cited

U.S. PATENT DOCUMENTS

| | | | |
|---|---|---|---|
| 6,021,093 A | 2/2000 | Birchak et al. | |
| 6,038,513 A | 3/2000 | Varsamis et al. | |
| 6,088,294 A | 7/2000 | Leggett, III et al. | |
| 6,125,079 A | 9/2000 | Birchak et al. | |
| 6,213,250 B1 | 4/2001 | Wisniewski et al. | |
| 6,366,531 B1 | 4/2002 | Varsamis et al. | |
| 6,552,962 B1 | 4/2003 | Varsamis et al. | |
| 6,564,899 B1 | 5/2003 | Arian et al. | |
| 6,672,163 B2 | 1/2004 | Han et al. | |
| 6,693,554 B2 | 2/2004 | Beique et al. | |
| 6,747,570 B2 | 6/2004 | Beique et al. | |
| 6,817,229 B2 | 11/2004 | Han et al. | |
| 6,891,777 B2 | 5/2005 | Pabon et al. | |
| 6,899,197 B2 | 5/2005 | Arian et al. | |
| 6,957,145 B2 | 10/2005 | Spross | |
| 6,987,463 B2 | 1/2006 | Beique et al. | |
| 6,995,500 B2 | 2/2006 | Yogeswaren | |
| 7,036,363 B2 | 5/2006 | Yogeswaren | |
| 7,046,165 B2 | 5/2006 | Beique et al. | |
| 7,075,215 B2 | 7/2006 | Yogeswaren | |
| 7,173,542 B2 | 2/2007 | Beique et al. | |
| 7,364,007 B2 | 4/2008 | Garcia-Osuna et al. | |
| 7,367,392 B2 | 5/2008 | Duong et al. | |
| 7,389,828 B2 | 6/2008 | Ritter et al. | |
| 7,418,865 B2 | 9/2008 | Griffiths et al. | |
| 7,460,435 B2 | 12/2008 | Garcia-Osuna et al. | |
| 7,513,147 B2 | 4/2009 | Yogeswaren | |
| 7,587,936 B2 | 9/2009 | Han | |
| 7,658,196 B2 | 2/2010 | Ferreri et al. | |
| 7,775,215 B2 | 8/2010 | Hassler, Jr. et al. | |
| 7,775,966 B2 | 8/2010 | Dlugos et al. | |
| 7,814,782 B2 | 10/2010 | DiFoggio | |
| 7,844,342 B2 | 11/2010 | Dlugos, Jr. et al. | |
| 7,927,270 B2 | 4/2011 | Dlugos et al. | |
| 7,932,834 B2 | 4/2011 | Beique et al. | |
| 7,950,451 B2 | 5/2011 | Alberty | |
| 8,016,744 B2 | 9/2011 | Dlugos et al. | |
| 8,028,767 B2 | 10/2011 | Radford et al. | |
| 8,057,492 B2 | 11/2011 | Ortiz et al. | |
| 8,066,629 B2 | 11/2011 | Dlugos | |
| 2006/0249307 A1* | 11/2006 | Ritter et al. | 175/40 |
| 2007/0205022 A1 | 9/2007 | Treviranus et al. | |
| 2007/0235199 A1 | 10/2007 | LoGiudice et al. | |
| 2008/0053707 A1 | 3/2008 | Martinez et al. | |
| 2008/0128175 A1 | 6/2008 | Radford et al. | |
| 2008/0186805 A1* | 8/2008 | Han | 367/35 |
| 2009/0266544 A1 | 10/2009 | Redlinger et al. | |
| 2009/0294173 A1 | 12/2009 | Laird et al. | |
| 2010/0089583 A1 | 4/2010 | Xu et al. | |
| 2010/0139981 A1 | 6/2010 | Meister et al. | |
| 2010/0282511 A1 | 11/2010 | Maranuk et al. | |
| 2011/0203849 A1 | 8/2011 | Radford et al. | |
| 2011/0226531 A1 | 9/2011 | Jones | |

* cited by examiner

DRILLING TOOL, APPARATUS AND METHOD FOR UNDERREAMING AND SIMULTANEOUSLY MONITORING AND CONTROLLING WELLBORE DIAMETER

CROSS-REFERENCE TO RELATED APPLICATIONS

This application is a continuation-in-part of WO 2009/PCT 156552 A1 and GB0811815.0 (Jun. 27, 2008) granted GB2460096.

FIELD OF THE INVENTION

This invention relates to an integrated expansion and caliper tool capable of simultaneously enlarging and measuring borehole and tubular diameters, especially, underreamed wellbores in the oil and gas industry. The expandable blocks of the tool can be configured with cutting or stabilising elements while the calipers can be acoustic sensors or mechanical gauge probes to measure the underreamed wellbore diameter. Further measurements can be obtained from a calibration sensor that measures fluid properties. Other measurements can be made by block positional sensors and vibration sensors independent of the former.

It is to be understood that the term 'expansion' as used herein refers to the capacity of the tool to expand outwardly and against the interior wall of a passage, such as a borehole, especially a wellbore, or a tubular used as a casing, and then to apply pressure or a cutting action against the wall. It is not always essential that the wall itself be expanded, since the tool can be used for centralisation or stabilisation or like purposes without necessarily expanding the passage.

When constructing an exploration or production well, numerous downhole operations are conducted to drill and measure the borehole so that it meets the desired dimensions specified in the well-plan. Drilling operations may utilize a reamer to ensure that the hole diameter that has been drilled by the bit is maintained within the given tolerance for the plan. The hole diameters drilled by the bit and perfected by the reamer are substantially the same. The maximum cutting diameter of the reamer, which is fixed, is substantially the same as the bit diameter. This maximum cutting diameter is defined by the pass-through diameter of any restriction in the borehole above the operating location.

In contrast to a reamer, an underreamer is used to enlarge the diameter of the borehole beyond its original drilled size. Enlargement (underreaming) is typically done below a restriction in the borehole, and the cutting diameter of an underreamer is always greater than that of the pass-through diameter of the restriction. Additionally, an underreamer is provided with activation and deactivation modes and mechanisms for extending and retracting cutting elements to ensure effective underreaming once it has passed below the restriction.

Measurement may involve the acquisition and communication to surface of various types of wellbore data such as resistivity, porosity, permeability, azimuth, inclination and borehole diameter or rugosity, formation dips or bedding angles.

Measurement itself occurs in two modes, either wireline or logging-while-drilling. Wireline is the most common measurement technique and is performed as a separate and consecutive activity to drilling, involving the conveyance of measurement tools on a wire or cable. Wireline calipers use a plurality of fingers to take borehole diameter measurements. However, wireline calipers can only take measurements in an axial direction. Due to this limitation, they can only be used after drilling otherwise the rotational and impact forces of drilling would cause them to break. Hence a separate caliper run is required after drilling to measure borehole diameter.

Logging-while-drilling tools may acquire various data from the wellbore. Acoustic calipers may be incorporated within logging tools such as neutron density tools. As they can be rotated, acoustic calipers may be used while drilling to acquire measurement data. However, almost all logging tools are configured as complete systems and are only available at very high cost and used in a low percentage of wells worldwide. Further they also suffer from limitations in applications with slide drilling, where a downhole motor rotates the bit and drags the drillstring and bottom-hole assembly (BHA). In rotary steerable applications the logging tools are configured near to the bit. Therefore, the location of the acoustic caliper is within the BHA below the underreamer at a considerable distance away from the underreamer.

Furthermore, prior art acoustic calipers are susceptible to erroneous time of flight readings due to changes in the density of drilling or wellbore fluids. The configuration and lack of calibrated in-situ density or sound time of flight fluid measurements present difficulties for prior art acoustic calipers.

Borehole measurements do not always rely on acoustic calipers. Actually, it is routine for borehole measurements to be taken in a separate activity after drilling or underreaming (wellbore enlargement) has taken place.

The time-lag associated with the separated operations of underreaming and measurement leads to uncertainty and unnecessary cost. In the case of underreaming, measurements are taken a posteriori, which means a separate caliper run and at times further corrective underreaming runs to attain the desired wellbore diameter.

BACKGROUND OF THE INVENTION

Oil and gas accumulations are found at depth in different geological basins worldwide. Exploration and production of such accumulations rely on the construction of a well according to a well plan.

Various well types exist and are defined according to usage such as wildcats or those used in exploration, delineation, and production and injection. Variations in well profile exist also according to vertical, slant, directional and horizontal trajectories. Each well differs according to the oil company's objectives and the challenges that a given basin presents from the surface of the earth or the ocean to reaching the hydrocarbon reservoir at a given underground depth.

Engineering challenges are related to the location of the well-site such as onshore or offshore, seawater depths, formation pressures and temperature gradients, formation stresses and movements and reservoir types such as carbonate or sandstone. To overcome these challenges, a highly detailed well plan is developed which contains the well objective, coordinates, legal, geological, technical and well engineering data and calculations.

The data is used to plot the well profile, and plan its execution using precise bearings, which is designed in consecutive telescopic sections—surface, intermediate and reservoir. To deliver the well objective and maintain the integrity and operating capacity of the well over its lifecycle, a given wellbore with multiple sections and diameters is drilled from surface. Although there are many variants, a simple vertical well design could include the following dimensions: a surface or top-hole diameter of 17½" (445 mm), intermediate sections of 13⅝" (360 mm) and 9⅝" (245 mm) narrowing down to a bottom-hole diameter of 8½" (216 mm) in the reservoir section.

Each consecutive section is 'cased' with a number of metal tubes placed into the wellbore with the specified diameter according to the length of the section. Casing tubes are connected to each other after which they are cemented into the outer wall of the well. In this way, a well is constructed in staged sections, each section dependent on the completion of the previous section until the well is isolated from the formation in question along the entire distance from surface to the reservoir.

Scarcity of oil and gas is driving oil and gas companies to explore and develop reserves in more challenging basins such as those in water-depths exceeding 6,000 ft (1800 m) or below massive salt sections. These wells have highly complex directional trajectories with casing designs including 6 or more well sections. Known in the art as 'designer' or 'close tolerance casing' wells, these wells have narrow casing diameters with tight tolerances and have created a need to enlarge the wellbore to avoid very narrow reservoir sections and low production rates.

Therefore, the bottom-hole assemblies that are needed to drill these wells routinely include devices to underream the well-bore below a given casing diameter or other restriction. In this way, underreaming has become an integral part of well construction and there is now an increased dependence on underreaming to meet planned wellbore diameters. After underreaming, the underreamer is tripped out of the borehole and replaced by the caliper, which is an instrument for measuring the internal dimensions of the wellbore either mechanically, using extended fingers that contact the wall of the wellbore, or by acoustic techniques using reflected acoustic signals from the wall of the wellbore.

Previously, the underreamer and caliper have been considered as two separate tools, each involved in distinct functions. Typically, an underreaming run could take 24 hours, after which a further 24 hours would be required for preparation of the caliper run. A further 24 hours could be taken in the caliper run before knowledge could be gained of actual wellbore diameters. This time-lag between underreaming and caliper measurements therefore could easily exceed 48 hours depending on the depths involved. If the actual hole diameter did not match the planned diameter, casing tolerances would not be met and a corrective run would be required. Consequently, the whole cycle of underreaming and caliper measurements would need to be repeated.

In other applications such as expandable tubular or increased cementing thicknesses, the tolerances between the enlarged well-bore and the expanded steel tube and cementing thickness are very close. Variations of 1" (25 mm) in the diameter can lead to the failure of the well construction activity.

SUMMARY OF THE INVENTION

The present invention has for a principal object to provide an improvement on the prior art in wellbore underreaming and wellbore measurement wherein the actual diameter of the underreamed hole is measured directly in real time, that is to say simultaneously with, or immediately after, a wellbore expansion operation.

The invention is based on an integrated underreamer and caliper tool or apparatus that is equipped with one or more means for measuring the underreamed wellbore diameter and calibrating said wellbore diameter measurements using drilling fluid properties sensors to provide real time performance verification, automated troubleshooting and delivery of desired wellbore diameters.

The present invention seeks to integrate and automate underreaming and caliper measurements and eliminates the need for separate caliper runs and minimizes the need for corrective underreaming runs by providing real-time data which allows the driller to respond earlier thereby saving time and money on wellbore operations.

It is thus an object of the present invention to provide underreaming expansion blocks integrated with calipers for measuring the underreamed wellbore diameter, enabling the tool to give immediate measurements of the accuracy of the wellbore-widening operation and, if the diameter is found insufficient or undergauge, to automatically detect and diagnose the potential faults, and to repeat underreaming until a satisfactory result is achieved.

Although underreaming is the principal route to wellbore diameter enlargement, the invention may be applied to alternative enlargement means integrated with measurement calipers that use bicentre bits, fixed wing bits, eccentric underreamers and expandable bits.

In one embodiment, the tool is capable of simultaneously conducting well-bore enlargement, taking caliper measurements using an acoustic echo-pulser and sensor, and verifying performance through a micro-processor that uses caliper measurements which are calibrated by means of drilling fluid properties sensors. This enables the tool to detect undergauge hole and conduct diagnostics according to a logic circuit. In this way, the user can achieve a planned or desired wellbore diameter and at any given time check that the underreamer is functioning correctly. Whenever a problem occurs and if the corrective steps have been taken and the caliper indicates that the desired hole diameter is still not being delivered a signal may be sent to the rig-surface or to the location of the operating engineer so that further remedial action can be taken, according to a logic circuit. This may include extending cutter blocks in response to caliper data, checking block positions or any number of logic steps. A memory card may store sensor information that can be downloaded at surface when the tool is retrieved, or sent to the surface by telemetry.

The tool may also have a built-in link to a mud-pulse telemetry system to allow real-time monitoring of the underreaming operation (caliper measurements, fluid properties calibration data and simultaneously cutter-block position). One or more mechanical calipers (gauge probes) or acoustic echo-pulsers may be optimally spaced in order to emit a number of sound waves during a given time period which are reflected back by the near wellbore or by the far formation in the case of a cavernous formation and picked up by a sensor installed in the same tool. The travel or transit time of the sound waves at a given speed can be processed by the microprocessor and integrated with calibration measurements in order to accurately determine the distance traveled and the wellbore diameter measurement.

A keyway may provide a channel for wiring from the sensors to the processor and transponder. The wiring can be used to transmit acoustic data retrieved by the acoustic sensors, the fluid properties calibration sensor as well as positional data from the mechanical blocks, to the processor. The processor can process this data and sends it to the transponder to be sent to the control system at the surface. The keyway may be sealed and filled with a means to absorb vibration such as silicone gel or grease and to maintain wires in position.

The transponder converts data sent by the processor so that it can be transmitted to the surface by means of the mud-pulser which uses a series of binary codes at a given frequency using drilling fluid as means of transmission. Other means of wireless transmission can be used, using radio frequency or electro-magnetic pulses. This allows up and downlink of the tool in order to receive and transmit data and commands. The data may be transmitted to the surface for use by the drilling operator or may be further transmitted by satellite to a remote operations centre.

One embodiment of the invention provides for a wellbore underreaming tool or apparatus, which is particularly applicable in oil and natural gas wells, arranged for attachment to a rotary drill-bit and associated drill-pipe, which comprises at least one radially extendable cutter block (62), at least one caliper (76 or 64-66) to determine the wellbore diameter, a fluid properties calibration sensor all of which are integrated within the body of the tool and inter-connected by means of a micro-processor to verify and control a desired wellbore diameter (22) through comparison and correlation of the simultaneous measurements from the caliper and the fluid properties calibration sensor.

The tool support may be the drill string but it may also be a length of coiled tubing.

The tool body is a cylindrical high grade steel housing adapted to form part of the bottom-hole assembly by means of a screw connection arranged at the end of the tool, which is coupled to the drill bit. The attachment need not be direct, but may be indirect, depending on the requirements of the different elements of each drill string and each well. The lower end of the BHA may be a drill bit, or a bull nose, and this part and the tool there may or may not be a means for directional control of the wellbore such as a rotary steerable system.

In one embodiment of the invention, the expansion operation is an underreaming application, and expansion elements comprise a set of cutter blocks optimally configured with cutter inserts and nozzles. In another embodiment, the expansion elements may comprise expansion blocks, which may be of similar construction to the cutter blocks, but having outer surfaces where cutter elements may be replaced by a hardened material. Such expansion blocks may simply bear under pressure against the inside of a tubular wall, with sufficient force to deform it outwardly to a larger diameter. In yet another embodiment, the same blocks may simply bear against the underreamed wellbore in order to stabilize the tool within the wellbore without enlarging the bore. The same blocks maybe received within an additional section of the tool or a separate steel body suitably prepared to provide a means of stabilization to the expansion operation. In a further embodiment, the same blocks maybe received within an additional section of the tool or a separate steel body suitably prepared as apparatus to provide a means of stabilization for underreaming applications.

In one embodiment where the wellbore expansion activity is underreaming the cutter blocks are situated within the tool body in an open chamber, the outer surface of which is composed of a plurality of high strength cutter elements such as polydiamondcrystalline inserts arranged externally. The cutter block is provided with a flow of drilling fluid via an external nozzle adjacent to the set of cutters which allows drilling fluid to flow from an internal bore connected to a source of said drilling fluid.

In another embodiment, the tool comprises a module that can be coupled by means of a thread connection to the body of the tool which comprises expandable stabilizing blocks in order to stabilize the tool against the wellbore walls during underreaming and measurement and if so required, increase or expand the diameter of the metallic tube casing of the well.

It is to be noted that the description herein of the expansion blocks is applicable generally, irrespective of the function of cutting, expansion or stabilization of the drill string. Thus, the cutter blocks are provided with cutting inserts or teeth to enable underreaming of the wellbore that may be replaced by hardened smooth surfaces for expansion operations of an expandable steel tubular inside the wellbore.

In one embodiment the microprocessor control means (68) are adapted to receive, during drilling operations, information simultaneously from the caliper for measuring the wellbore diameter and from fluid properties sensors as well as the positional sensors of the extendable cutter block in order to control the extension and retraction of said block in response to caliper data or according to the logic circuit in order to detect and correct failures in real-time and achieve the desired wellbore diameter.

The tool normally comprises a plurality of such cutter blocks, arranged symmetrically around the tool. Two cutter blocks would be on opposite sides of the tool, three blocks would be separated by 120 degrees, four blocks by ninety degrees, and six by sixty degrees. In operation, the tool is typically rotated together with the drill string as well as being moved axially along the wellbore.

The tool body is provided with an internal bore for receiving drilling fluid via a device nozzle adjacent the cutter. In each case, the nozzles provide a fluid flow that help to keep the cutters clean and prevent the build-up of clogging debris from the underreaming operation and provide a cooling and lubricating function for the cutters. In one preferred aspect of the present invention the tool incorporates a non-mechanical means of measurement such as an acoustic caliper for measuring the underreamed wellbore diameter.

The calipers for measuring the underreamed wellbore diameter with which the underreamer is equipped emit sound pulses that are reflected from the wellbore walls. These reflected echoes are used to calculate the distance by multiplying time by the propagation speed of the acoustic pulse or the sound transit time. The underreamed wellbore diameter calipers are generally located in the tool body above the underreamer but in an alternative configuration of the tool may be placed within the cutter block itself in the most radially extended zone among the cutting elements.

In a further embodiment, the invention provides for a method of operating an expansion tool or apparatus to underream a borehole to a desired dimension below a restriction, which comprises locating said tool or apparatus in said borehole on drill-pipe below a restriction, measuring the wellbore diameter by the caliper means, simultaneously calibrating said caliper measurements, extending a set of cutter blocks to an expansion diameter greater than the restriction, rotating the tool and moving it axially along the borehole on the drill string or other support, measuring wellbore diameter by said caliper means and continuing underreaming until the desired dimension is achieved.

In accordance with the method of the invention, the tool may be provided with expandable cutter control means responsive to dimension data received from the caliper means. In this way, an integrated tool and apparatus which is capable of diagnosing under-performance and correcting it may be realized. The dimension data may prompt for tests and checks on the effective deployment of the expandable blocks, may trigger a repeated cycle of expansion, or activate a further set of cutters and may provide data to a surface monitor to signal an opportunity for operator intervention.

Thus, in the case of an underreaming tool with acoustic caliper means, acoustic reflections from an echo-pulser may be transmitted to a sensor and calculated as distance by multiplying time by speed. The processor correlates the borehole data from the fluid properties sensor allowing for variations in fluid or formations. The processor uses this data to correlate whether the pre-programmed wellbore diameter is actually being underreamed and measured. Where the processor detects a fault or difference between the two minimum measurements it automatically troubleshoots the fault using a logical procedure.

The skilled operator will readily appreciate that other procedures may be implemented by the logic circuit or control program within the tool's processors, which can be programmed to cover other scenarios.

BRIEF DESCRIPTION OF THE DRAWINGS

The various embodiments of the invention are illustrated by way of non-limiting examples in the accompanying drawings, in which.

DETAILED DESCRIPTION OF THE INVENTION

Figure 1:
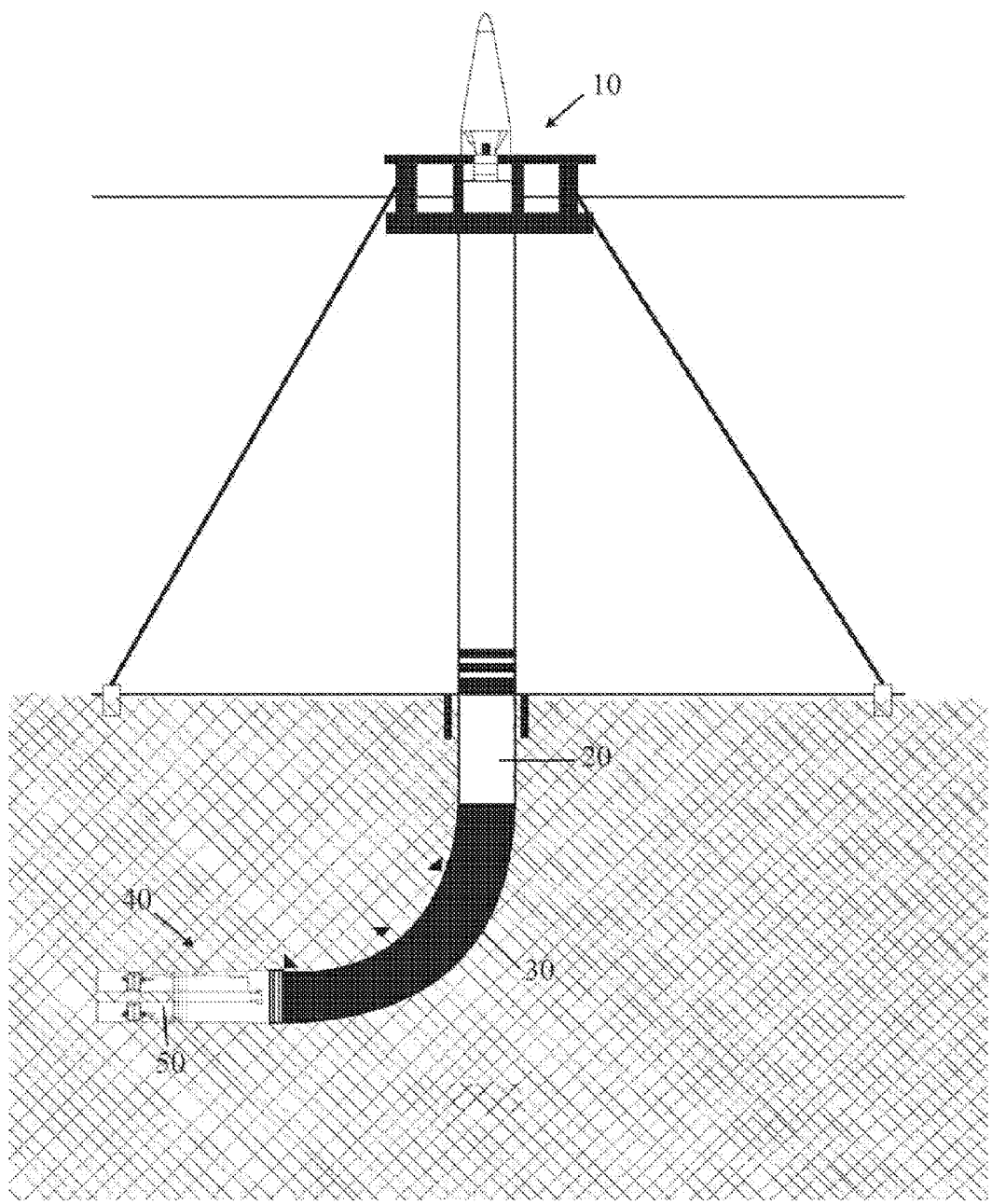
FIG. 1 is a general diagrammatic view of an oil or gas well showing surface structures and the interior of the underground wellbore, with a tool in accordance with the invention as part of the final bottomhole assembly.

As shown in FIG. 1, an exploration or production rig comprises a surface structure (10) at the wellhead, a wellbore (20), a drill string (30) in the wellbore and a bottom-hole assembly (40) at its lower end where the tool or apparatus (50) may be configured according to the present invention with the desired configuration of modules: module housing the expandable cutter blocks, module housing the calipers, sensors and processors and the module with expandable stabilizer blocks or expandable blocks to expand a tubular within the wellbore. The tool or apparatus (50) comprises at least one underreamer module integrated with a wellbore diameter measurement caliper tool incorporating a sensor to measure fluid properties and calibrate said caliper measurements, and capable of connection to a drill-bit.

Figure 2:
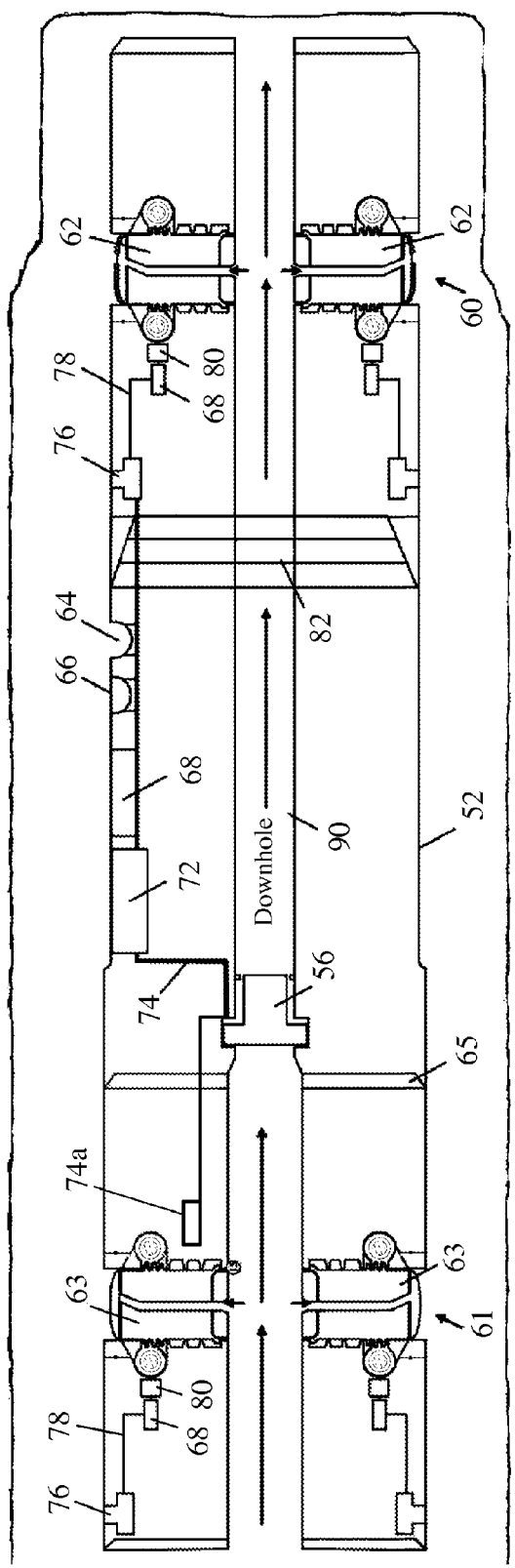
FIG. 2 is a longitudinal section of the tool and apparatus according to one embodiment showing the expansion elements constituted by both cutter blocks and stabilizer blocks in a deactivated state.

The longitudinal section of the tool illustrated in FIG. 2 comprises a steel tool body (52) provided with an internal flowbore (90) and a mud-pulser (56), which is adapted to be engaged by a further drill collar (not shown) to connect it to the other elements of the bottom-hole assembly (40), and then to the drill string (30) as required by the drilling operation.

The tool body is also provided with elements for cutters (60) and stabilizers (61), a wellbore diameter measurement caliper (76 or 64-66) uphole of the cutter blocks (62). The expandable cutter (60) is composed of various cutter blocks (62) placed symmetrically and radially outwards of the tool body (52) as shown in FIG. 2 in the de-activated status with the blocks retracted inside the tool.

In one embodiment the tool incorporates an acoustic caliper comprising an acoustic transmitter and receiver which can be housed within the body of the tool in sealed recesses (64 and 66 or 76). Tool performance is verified using the microprocessor (68) that compares data recorded by the acoustic receiver (66 or 76) with the programmed wellbore diameter, thus detecting possible undergauge hole diameters. The tool is automated according to logic control sequences stored in each processor (68) to deliver a desired wellbore diameter and in order to ensure the underreamer is functioning correctly. Once verification and corrective steps have been taken, and if the caliper for measuring the underreamed wellbore diameter (66 or 76) indicates that the required hole diameter is still not being delivered, a signal is sent via the mud-pulser (56) to the rig-surface (10) to allow control commands to be sent by the operator either locally or by remote control. These control commands adopt the relevant operative and corrective measures such as modification of the pump flow rate of mud or drilling fluid, activation of cutter blocks in response to caliper data, replacement of the bottom-hole assembly etc. The memory card associated with the processor (68) stores data from the calipers, fluid properties measurement sensors. The said data is transmitted in real time in order to be used in the underreaming and drilling operations (56) or physically downloaded by removing said card when the tool is retrieved from the well.

The tool is provided with a built-in link to the telemetry system (56) which also serves to monitor performance of the under-reaming operation, position of expansion blocks (62) and data recorded by the caliper for measuring the underreamed wellbore diameter (66 or 76) as well as data from the fluid properties sensor. One or more acoustic sensors (64 or 76) are placed within the tool body (52) in order to emit a number of sound waves during a given time period which are reflected back by the wellbore wall (FIG. 3, 22) and picked up by the receiver sensors (66 or 76). The processor (68) calculates the distance using transit time and calibrates transit time with data from the fluid properties sensors to establish the speed of return of the acoustic waves and wellbore diameter. The processor compares the measured wellbore diameter to the programmed desired diameter. If the two measurements match given user-defined tolerances the tool continues to operate to the total depth of the wellbore section to be underreamed. Where the measurements do not match the processor automatically activates a series of logic steps to troubleshoot the fault.

As further shown in FIG. 2, a keyway (74) provides a channel for wiring of the acoustic pulsers or transmitters (64 or 76) and the acoustic sensor/receivers (66 or 76) to the processor (68), and also to the transponder (72). In one embodiment the wiring is used to transmit acoustic data retrieved by wellbore calipers and fluid properties sensors as well as positional data from the cutter and stabilizer blocks to the processors and transponders. The keyway may be sealed and filled with a means to absorb vibration such as silicone gel.

The transponder (72) converts data from the processor (68) so that it can be transmitted to surface (10) via the mud-pulser (56) which transmits the data to surface using a series of binary codes at a given frequency using the drilling mud itself as means of transmission. Other means of wireless data transfer may be used such as systems using radio frequency or electro-magnetic pulses.

FIG. 2 also shows an alternative location for the caliper for measuring the underreamed diameter which may be a caliper (76) arranged in an encapsulated recess connected to wiring in keyway (74) connected to the processor which may also be connected to the acoustic (transmitter/receiver) calipers (66-64) and a new keyway connection (78) which may be connected to an alternate processor (68) which controls an activation motor (80) for the expandable block (62 or 63). FIG. 2 also shows an internal flow bore or axial through passage (90) in the tool to allow mud to flow through the whole bottom-hole assembly (40). The encapsulated recesses (64, 66 and 76) may also be used to house other types of sensors such as a vibration sensor to detect stick-slip conditions.

The tool or apparatus may be configured in three modules integrated by means of screw connections (65) and (82). The body of all parts of the tool or apparatus (52) is a cylindrical high grade steel housing adapted to form part of the bottom-hole assembly (BHA) (40) via internal screw connections to ensure the through flow of drilling fluid (90). The connection may be direct or indirect depending on the needs of the different drilling components of each BHA and each well. At the leading downhole end of the BHA there may be a drill-bit or a stabilizer and between this point and the tool there may be a wellbore directional control system. The stabilizing blocks (63) are constructed identically to the cutter blocks (62), except that in place of cutter elements (60) there is a surface which is hard faced (61) or coated with a hard abrasion-resistant material.

The hard faced surfaces of the stabilizer expansion blocks act to stabilize the drill string and eliminate some of the problems associated with the loss of directional control above the underreamer when the diameter in said zone is equal to that of the underreamer or greater than the pilot hole. Likewise, the tool can be used to expand or enlarge the diameter of metal tubes by deformation of the latter in the wellbore. In this case, the tool body facilitates the operation of expanding or enlarging the diameter of the expandable casing and is connected to the downhole assembly by means of a screw connection in said body.

The stabilizer module may be directly or indirectly connected to the underreamer and hard-wired accordingly (74a) to send data from the processor (68) to the transponder (72) through the mud-pulser (56) to surface.

Figure 3:
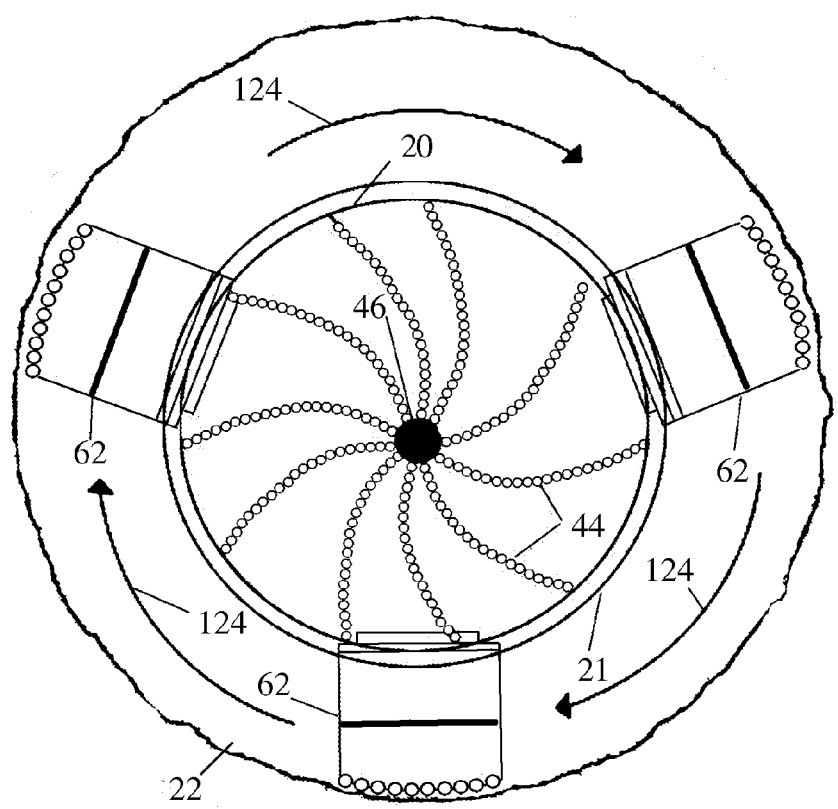
FIG. 3 is a cross section of the tool as seen from the drill bit, showing the diameters of the drill bit, of the pass-through casing and of the desired underreaming of the wellbore in accordance with the invention shown in the previous Figures, in the operative mode of the expanded expansion cutter blocks (activated operating mode)

FIG. 3 shows an uphole front view of the bit illustrating the generally designated expandable cutters (60) in the activated mode, i.e. with cutter blocks (62) expanded outwardly of the tool body and supported against the underreamed wellbore wall (22) which arises from the wellbore (20) which has not been underreamed. FIG. 3 shows the arrangement of the drill bit teeth in which there are ten curved rows of cutters (44), with cutter teeth in each one. A central drilling fluid outlet (46) indicates where drilling fluid passes through the internal flowbore (90) in the tool body (52). The direction of rotation of the bottom-hole assembly and of the drill bit is shown (124).

Figure 4:
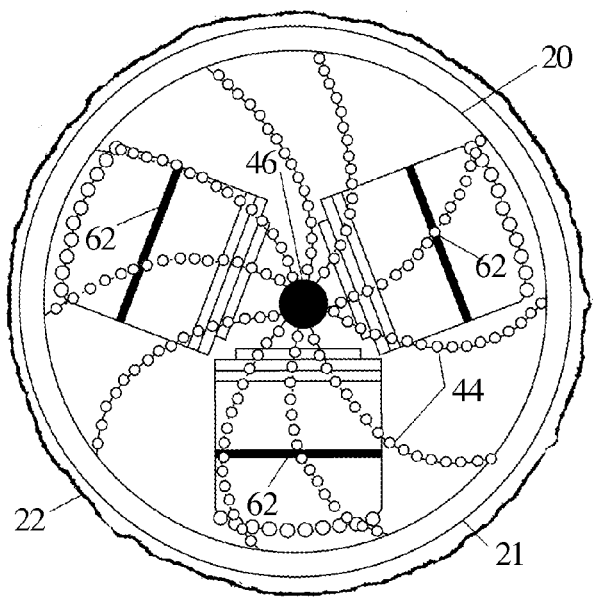
FIG. 4 shows a cross-section of the tool as seen from the drill bit, showing the diameters of the drill bit, of the casing and of the desired underreaming of the wellbore, according to the invention shown in earlier figures in the operative mode of the retracted expansion cutter blocks (deactivated operating mode)

FIG. 4 illustrates the same front view as FIG. 3 with the expandable cutters (60) in a deactivated condition, i.e. with cutter blocks (62) retracted within the inner chambers of the tool body without exceeding the wellbore diameter that has not been underreamed (20).

In one embodiment the caliper data itself from the underreamed wellbore diameter caliper is calibrated using measurements from the fluid properties sensors. The transit times of the fluid properties sensor is used to detect whether there is any change in wellbore or drilling fluid properties which would require caliper measurements to be calibrated. When the processor detects a difference between calibrated measurements, the processor automatically corrects the transit time of the caliper to ensure an accurate measurement.

Figure 5:
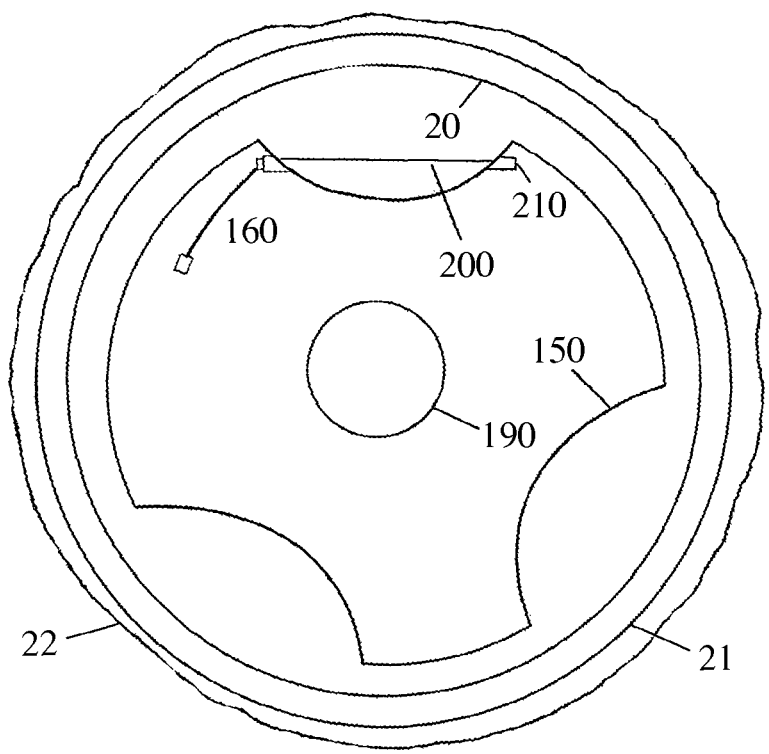
FIG. 5 shows a cross-section of the body of the tool showing longitudinal open channels which allow drilling or wellbore fluid to pass through and where the fluid properties transmitter or sensor device is placed.
Figure 5A:
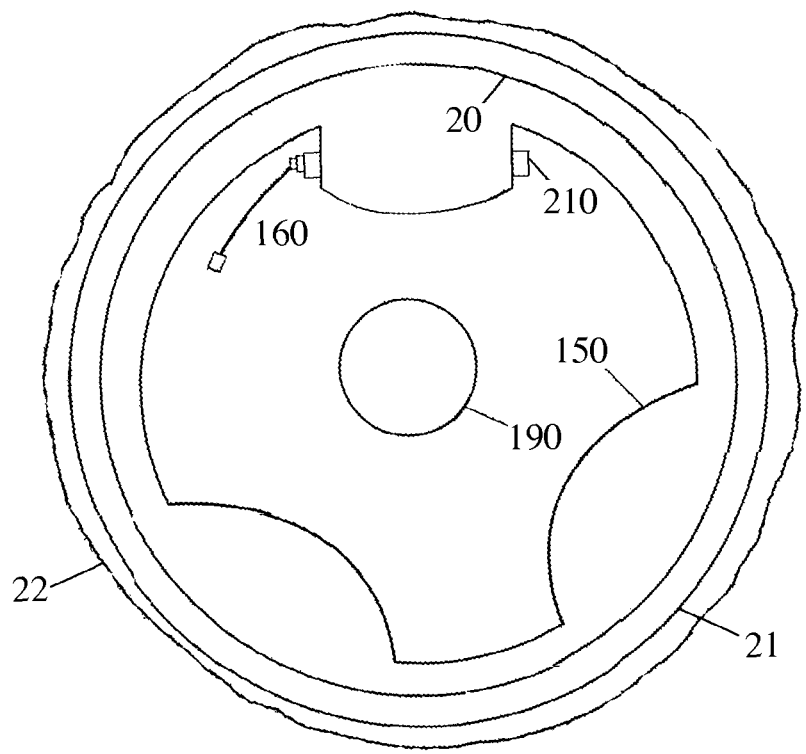
FIG. 5b corresponds to FIG. 5 and shows an alternate embodiment of a longitudinal open channel especially suited to an integrated transmitter/receiver (transducer).

FIG. 5 shows longitudinal open channels (150) known as "junk flow areas" where drilling fluid passes freely and incorporating fluid properties sensors. At least one transmitter (210) and a sensor/receiver (160) are located at two fixed points facing each other, preferably embedded within these channels and connected to a microprocessor in order to permit the measurement of fluid properties. In this way, for example, changes in sound transit time or the density of the fluid can be measured as the fluid passes through these channels during drilling operations or as it remains in the channels during non-drilling operations. The processor detects changes in the transit time or density of the drilling or wellbore fluid and calibrates the acoustic caliper measurements accordingly. FIG. 5 *b* corresponds to FIG. 5 and shows an alternate embodiment of a longitudinal open channel especially suited to an integrated transmitter and receiver (transducer).

In a further embodiment of the invention, caliper measurements are not only calibrated by means of fluid properties sensors but are compared with extended block positions. In this embodiment each expandable block is provided with lines or magnetic strips that allow a sensor to detect the actual position of the blocks. The magnetic signal is at its strongest when the block is fully extended and the magnetic line and sensor are aligned. In this way, it can be seen whether the block has actually been extended and determine its extension length and position. This block positional data is sent to the processor where it is stored, compared and correlated with the caliper data to deliver a desired wellbore diameter and also troubleshoot causes of failures. It is not necessary for the block positional sensor to be on the block itself and in an alternate embodiment the sensor may be on the housing itself as the purpose is to establish the relative position of the block to the tool.

As noted above, the invention provides a method of real-time drilling operation and control, which uses an extendable tool to underream the borehole to the desired dimension passing through a restriction, activating the tool, extending the extendable cutter block to a diameter greater than that of the restriction, rotating the tool and moving it axially along the borehole, enabling the simultaneous measurement and calibration of the borehole diameter by the caliper for measuring the underreamed wellbore diameter. Microprocessors connected to a control area act in response to data received from the caliper for measuring the underreamed wellbore diameter, the calibration fluid properties sensor with the objective of achieving the desired wellbore diameter and eliminate causes of errors or failures and minimizing drilling time by not tripping in with another caliper or performing further underreaming corrective runs.

Figure 6:
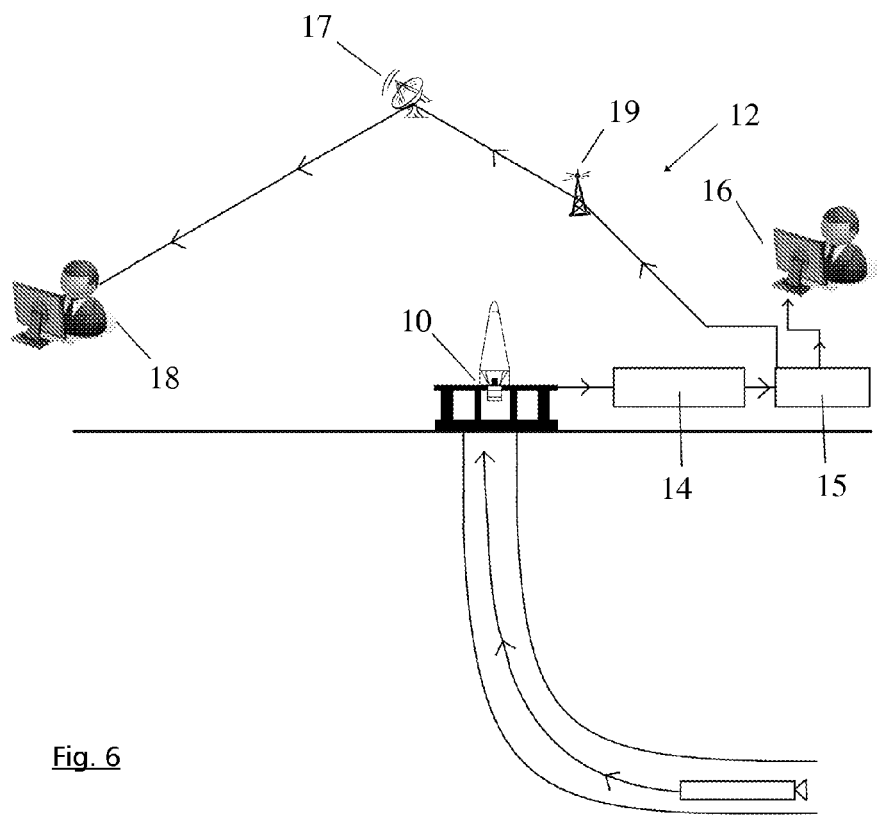
FIG. 6 is a general view of the well illustrating telemetry of the underreaming and drilling data recorded by the tool or apparatus.
Figure 7:
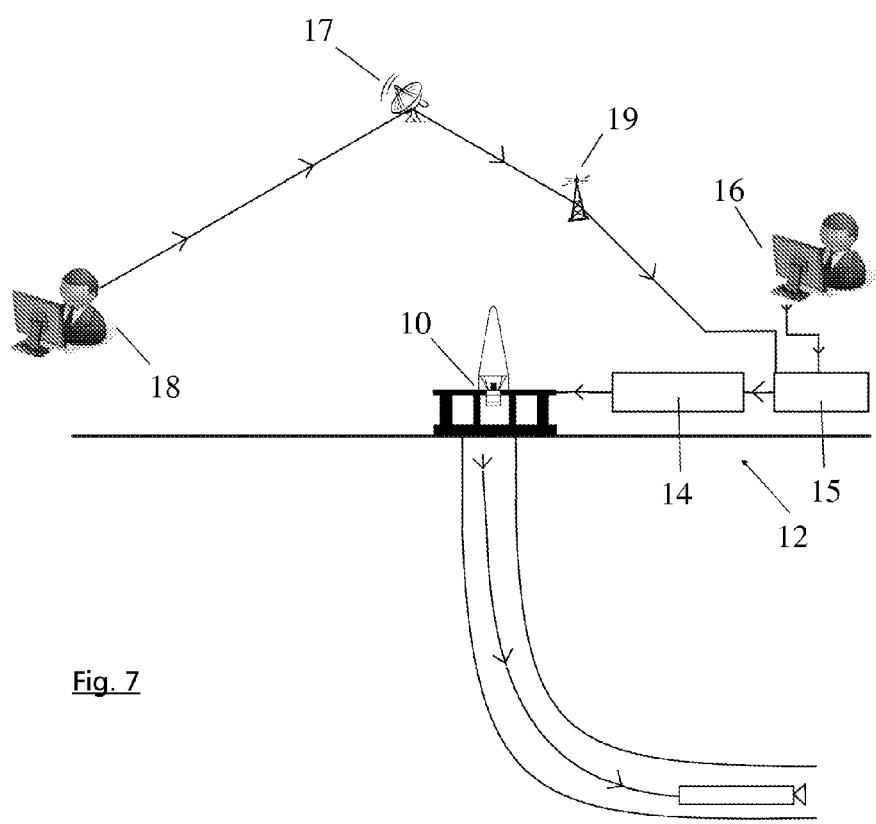
FIG. 7 corresponds to FIG. 6 but illustrates downlink telemetry of the data with parameters sent in order to control the underreaming and drilling by the tool or apparatus.

FIGS. 6 and 7 illustrate how the underreaming tool may utilize means for communicating data from the caliper for measuring the underreamed wellbore diameter, the calibration fluid properties sensors, the block positional sensors or the vibration sensors and control signals between the tool and a surface interface which may, among other functions, control the advance and trajectory of drilling during the underreaming operation.

As shown in FIGS. 6 and 7, the wellhead surface structure (10) includes a control and communications system (12) having an interface for telemetry with downhole instrumentation including a data processor or data logger (14) and a controller (15) which decodes binary codes from the mud pulser and may be linked directly to the user's drilling terminal (16). The decoded data may be yet further transmitted by satellite (17) beyond the wellhead to a remote operations centre (18) where another user of the drilling software may access the data and the control by means of a telecommunication link (19).

Figure 8:
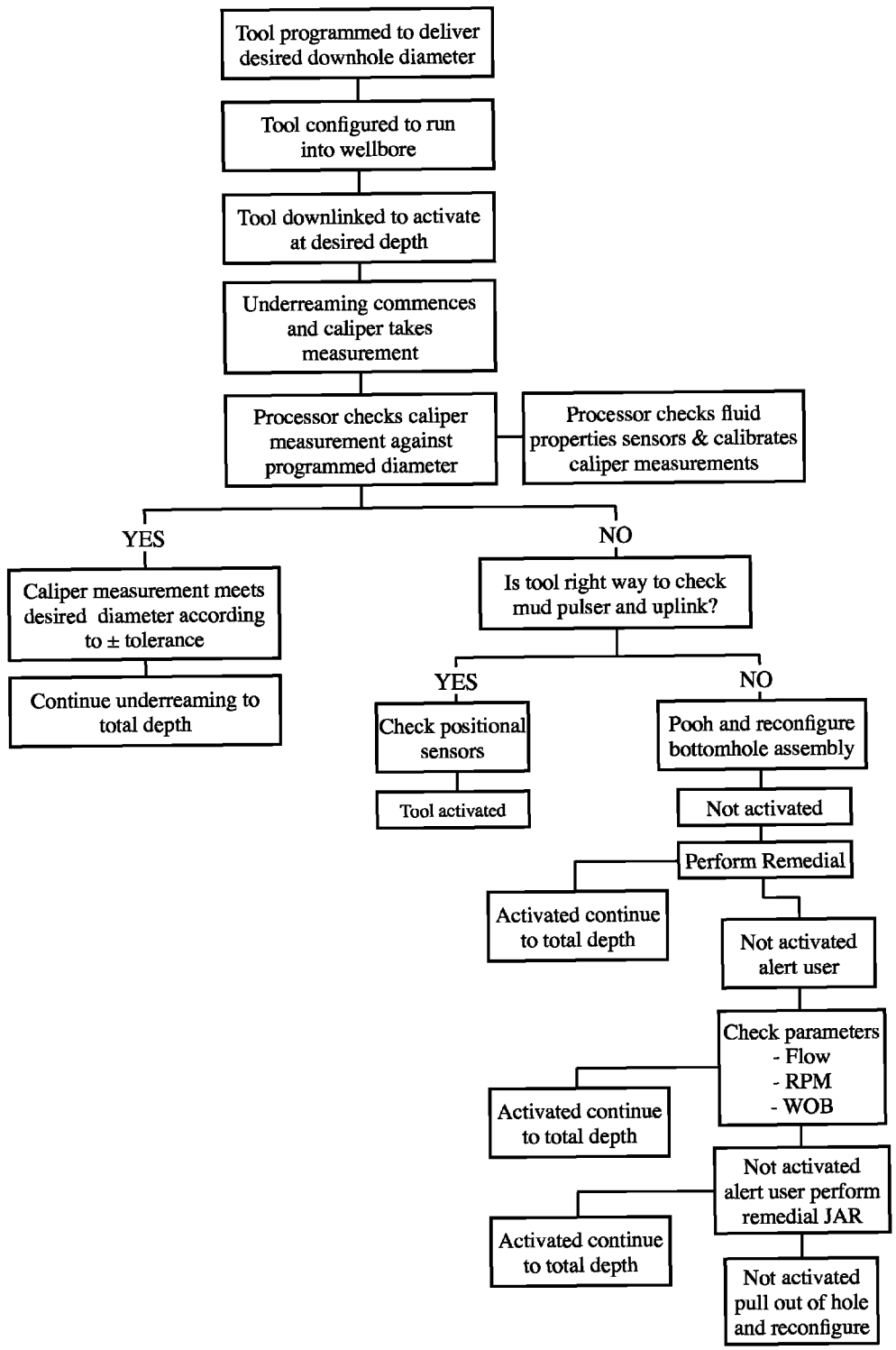
FIG. 8 is an algorithm and shown as an exemplary diagnosis and troubleshooting procedure for operational aspects of the underreaming and measurement of the drilling variables according to the invention.

FIG. 8 shows a logic diagram, with a control algorithm that may be configured in any number of ways so as to optimize performance.

An exemplary configuration involves a circuit to first cross check measured underreamed wellbore data using the caliper with the recorded block position data. If the block has been extended by means of the control system yet the data from the caliper for measuring the underreamed wellbore diameter shows that the actual wellbore diameter is below the planned diameter, the processor (68) activates the transponder (72). The transponder communicates with the control area (15) by means of the mud pulser (56) and corresponding decoder (16) to alert the user either on the rig (16) or at a remote centre (18) in which case communication is made through remote data transmission (17 and 19). The user is alerted to check drilling operational parameters and verify the actual underreamed wellbore diameter with that of the desired diameter.

Figure 9:
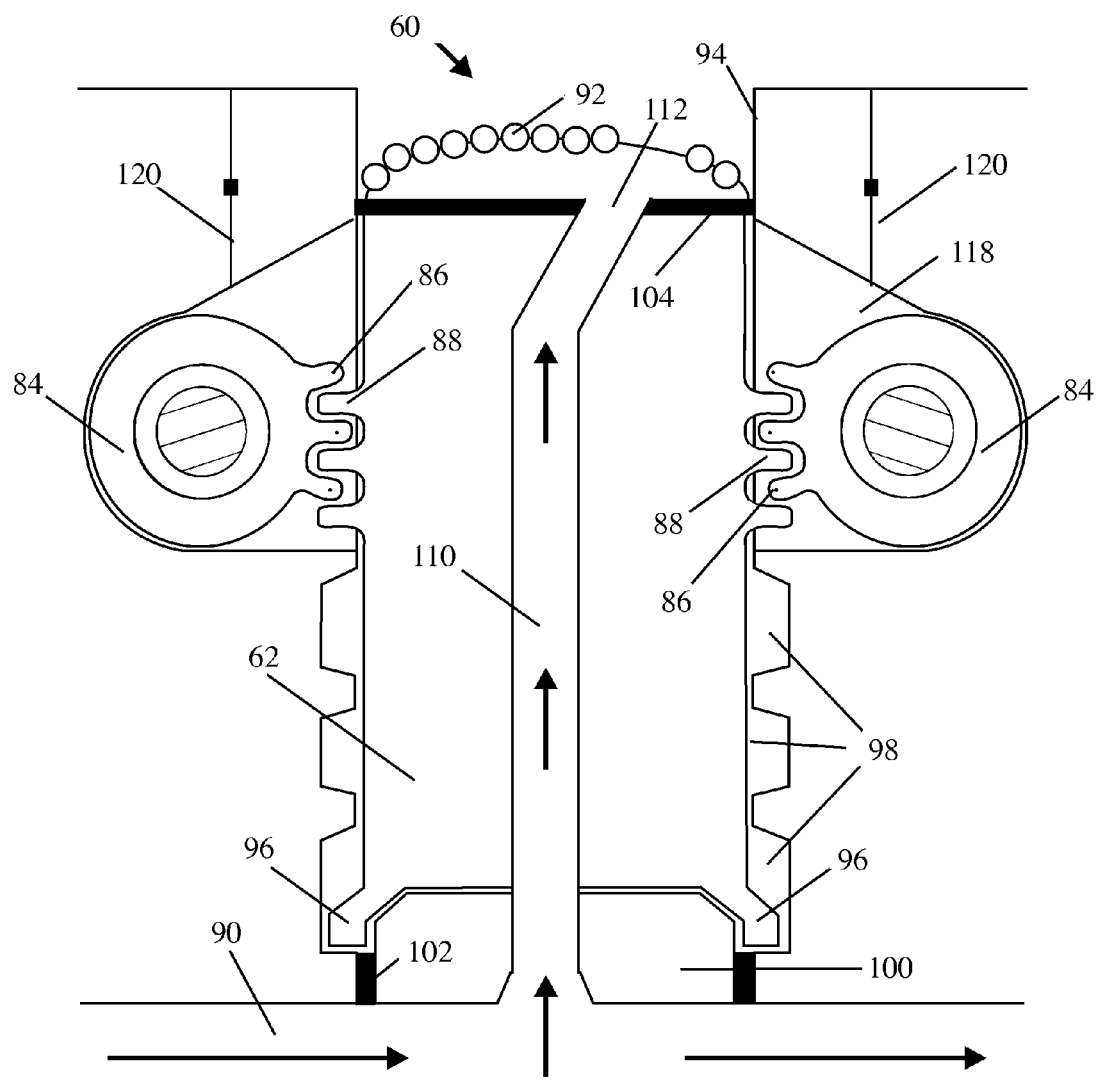
FIG. 9 is an enlargement of part of FIG. 2 showing an expansion block configured with cutters.
Figure 10:
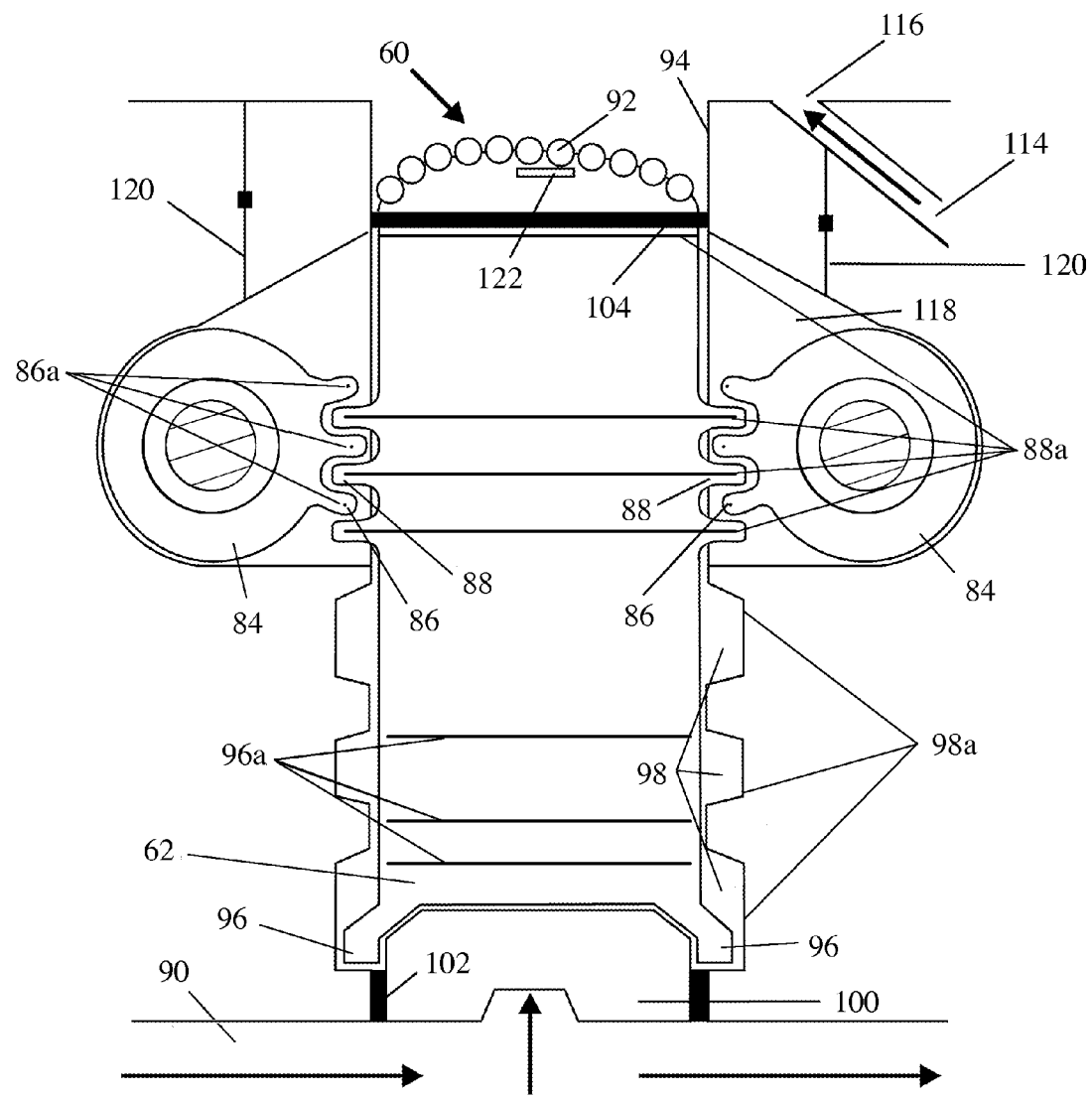
FIG. 10 is a view corresponding to FIG. 9 showing an alternative construction with external nozzle.

As shown in FIGS. 9 and 10, the illustrated examples are of two embodiments of the tool sharing common features which is an underreamer that uses a microprocessor (68) and electronic means to determine and control block position. According to these embodiments of the invention, caliper measurements are not only calibrated by means of fluid properties sensors but each block is provided with lines or magnetic strips that allow a sensor to detect the actual position of the blocks. The magnetic signal is at its strongest when the block is fully extended and the magnetic line and sensor are aligned. In this way, it can be seen whether the block has actually been extended and determine its extension length and position. This data is sent to the processor where it is stored, compared and correlated with the caliper data. Sensors on the block or housing (88a, 86a) determine the actual position of blocks (84) and send corresponding signals back to the processor (68). Suitable sensor means include detectors for a magnetic strip, respectively on the cutter block (88a or 96a) and housing (86a or 98a). It is to be noted that the following description of the cutter means is equally applicable to the structure and function of the stabilizer and expansion means in the uphole section (61) of the tool, with due allowance for the absence of cutter elements (92).

A set of cutters comprises at least one cutter block (62) carrying a plurality of cutter elements (92) directed outwardly of the tool body (52). The cutter block is received within the tool body in a cutter block chamber (94) having an open mouth, and the cutter is extendable from the chamber through the chamber mouth with the cutter elements projecting from the tool body, and retractable back into the chamber. A seal (104) is provided around the cutter block at the mouth of the receiving chamber (94).

As noted above, in one embodiment the tool is provided with means for extending and retracting the cutter block from and into the cutter block chamber, such means may comprise a power mechanism (84) in the tool body in engagement with driven teeth (86) on the cutter block. Motor means (80) are provided for extending and retracting the cutter block, and microprocessor control means for the motor means are both mounted within the tool body. The microprocessor control means is suitably adapted to receive bore dimension information from the caliper means (66) and to control the cutter block extension in response thereto. A mechanical lock is provided by means of a locking collet finger (96), which can be located into one of a plurality of retaining lip grooves (98) by travelling lock (100), which is located by sealing collar (102). The tool may be activated by means of electronic signal sent by mud-pulse and decoded or by other means using fiber-optics or wireless transmission.

Hydraulic locking means may be provided to resist retraction of the extended cutter block (62) into the cutter block chamber (94) when the extension of the cutter block is opposed by external pressure. This may comprise a port (not shown) open to a source of drilling fluid (passage 90) onto the travelling lock (100) immediately behind the cutter block.

The tool normally comprises a plurality of such cutter blocks (62), arranged symmetrically around the tool. Two cutter blocks are on opposite sides of the tool, three blocks are separated by 120 degrees, four by 90 degrees, and six by 60 degrees. In operation, the underreaming tool (50) is typically rotated on the drill string as well as being moved axially along the wellbore.

In accordance with an embodiment of the invention, shown in FIG. 9, the cutter block is provided with an internal flowbore (110) leading drilling fluid from a through passage (90) to an external nozzle (112) among the cutter elements (92). The source of drilling fluid may be the rig pumps via the drill-string (30) to the passage (90) for the flow of drilling fluid from the drill string to the drill bit. In another embodiment, as shown in FIG. 10, the tool body may be provided with an internal flowbore (114) leading drilling fluid from passage (90) to an external nozzle (116) adjacent the set of cutters. In each embodiment, the nozzle provides an optimized fluid flow that can help to keep the cutters clean and prevent the build-up of clogging debris from the underreaming operation, remove such material altogether from the underreaming zone, and provide a cooling and lubricating function for the cutters.

Figure 11:
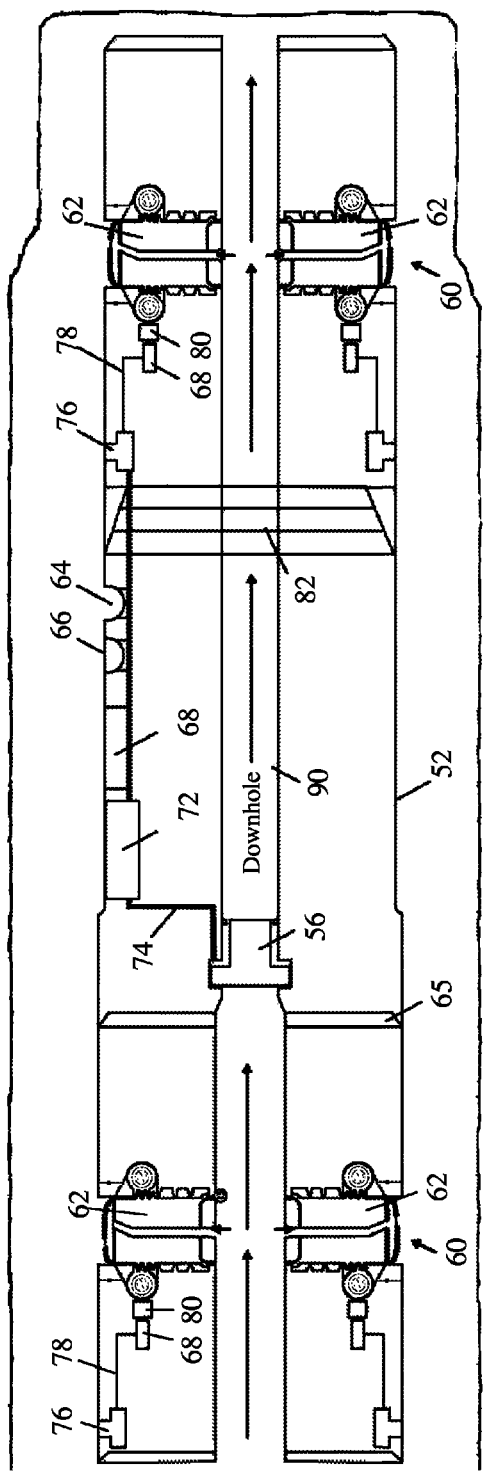
FIG. 11 is a longitudinal section of one embodiment of the tool or apparatus showing the expansion elements constituted by a set of cutter blocks and a further set of cutter blocks in a deactivated state.

FIG. 11 shows a further embodiment of the tool wherein a set of cutters is shown at the downhole end and a further set of cutters are shown at the uphole end, both sets of cutters suitably housed in modules. Such an embodiment comprises more than one set of expandable cutter blocks (62 and 62) integrated within independent modules that are screwed to each other, with the objective that one module comprises a set of cutter blocks that adapt their expansion to the actual underreamed borehole diameter and that another module has a set of cutter blocks extended based on wellbore diameter data received from the caliper in order to reduce drilling downtime.

Those skilled in the art will appreciate that the examples of the invention given by the specific illustrated and described embodiments show a novel underreaming tool and apparatus integrated with a caliper and accompanied by a method for underreaming verification and measuring underreamed wellbore diameter measurements using calibrated downhole fluid property measurements for accurate wellbore diameter measurements. A further embodiment includes a sensor for measuring the position of extendable blocks. While a further embodiment incorporates a vibration measurement sensor. Consequently, numerous variations are possible to achieve the purpose of the invention which is to improve drilling efficiency and provide certainty whenever a desired underreamed wellbore diameter is required. These embodiments are not intended to be limiting with respect to the scope of the invention. Substitutions, alterations and modifications not limited to the variations suggested herein may be made to the disclosed embodiments while remaining within the purpose and scope of the invention.

What is claimed is:

1. A wellbore underreaming tool for use in oil and natural gas drilling arranged for attachment to a rotary drill-bit and associated drill-pipe to enlarge the wellbore to a diameter greater than a pass-through diameter of a wellbore restriction, the underreaming tool comprising:
   at least one radially extendable cutter block to form the enlarged wellbore diameter;
   at least one caliper to determine the wellbore diameter;
   a position sensor to sense a relative position of the cutter block to a tool body;
   at least one calibration sensor to measure and detect changes in fluid properties, the at least one calibration sensor sensing fluid properties from one of a group comprising flow, rpm, weight, and hydraulic force; and
   at least one processor inter-connecting the at least one caliper and the at least one calibration sensor, said processor providing verification and control of a desired wellbore diameter by comparing simultaneous measurements from the caliper measuring wellbore diameter and from the position sensor for sensing the relative position of the extendable cutter block to the tool body, and compensating the measurements using said calibration sensor.

2. The underreaming tool as claimed in claim 1, further comprising:
   at least one extendable stabilizer block to stabilize the underreaming tool during expansion.

3. The underreaming tool as claimed in claim 1, in which the processor is adapted to receive and send information to a transponder housed within a caliper tool body from the caliper and the at least one calibration sensor to determine underreamed wellbore diameter and control extension of said block in response to caliper data to achieve a desired wellbore diameter.

4. The underreaming tool as claimed in claim 1, in which the processor receives and sends information to a transponder housed within the tool body from said caliper and the at least one calibration sensor as well as from the position sensor to control the extension of said block in response to obtained data from the caliper or the position sensor to achieve said desired wellbore diameter.

5. The underreaming tool as claimed in claim 1, in which the at least one calibration sensor includes a transmitter and a receiver located at two fixed points, facing each other and embedded within open longitudinal channels in a caliper tool body to permit the measurement of the fluid properties.

6. The underreaming tool as claimed in claim 5, further comprising: the at least one calibration sensor measures fluid properties selected from the group consisting of: drilling fluid density, drilling fluid sound transit time during drilling operations, drilling fluid sound transit time during non-drilling operations, and wellbore fluid sound transit time.

7. The underreaming tool as claimed in claim 2, further comprising:
   a plurality of sets of expansion elements integrated within independent tool modules, the first module comprising a first said set of cutter blocks that adapt their expansion to the actual borehole diameter, and the second module comprises a second set of stabilizer blocks that stabilize the tool against a wellbore wall during expansion.

8. The underreaming tool as claimed in claim 1, further comprising:
   a plurality of sets of expansion elements integrated within independent modules, the first module comprising a first said set of cutter blocks that adapt their expansion to the actual borehole diameter, and the second module comprises a second set of cutter blocks extended in response to feedback from caliper to deliver said wellbore diameter and reduce drilling downtime.

9. The underreaming tool as claimed in claim 1, wherein the extendable cutter block is placed within an open chamber in the tool body and is composed of high strength cutting elements arranged externally and receiving drilling fluid from a source of drilling fluid to an external nozzle placed adjacent to said cutting elements.

10. The underreaming tool as claimed in claim 1, further comprising:
    a telemetry device for communicating data from the caliper for measuring the wellbore diameter, and the position sensor measuring the position of the at least one extendable cutter block, and control signals between the underreaming tool and a control area provided at surface to permit an operator to optimize drilling performance in real-time.

11. The underreaming tool of claim 1, further comprising:
    a calibration channel and a mechanism to determine in-situ properties of wellbore fluids using a transducer and the at least one processor to measure said wellbore fluid properties between two fixed points facing each other and located within said calibration channel.

12. The underreaming tool of claim 11, wherein said wellbore fluid is drilling mud and the sensed in-situ property is drilling mud density.

13. The underreaming tool of claim 12, wherein said mechanism is an acoustic caliper and the sensed in-situ property is sound transit time.

14. The underreaming tool of claim 13, wherein said acoustic caliper includes a mud-pulser.

15. The underreaming tool of claim 12, wherein said calibration channel is within a junk slot area, and the transducer is located in the junk slot area.

16. The underreaming tool of claim 1, wherein the underreaming tool outputs the desired wellbore diameter, and wherein the desired wellbore diameter is selected from the group consisting of: cementing thickness, casing tolerance, a well section isolated from the formation, and a well isolated from the surface to a subsurface reservoir.

17. The underreaming tool of claim 1, wherein the underreaming tool outputs a desired wellbore diameter, and wherein the desired wellbore diameter is selected from the group consisting of: expandable tubular expansion, expandable tubular cementing thickness, expandable casing tolerance for an expandable tubular, a well section isolated from the formation, and a well isolated from the surface to a substitute reservoir.

18. The underreaming tool of claim 10, further comprising:
at least one pressure signal generated during underreaming.

19. The underreaming tool as claimed in claim 1, wherein the drill-bit is replaceable by a bullnose, and wherein said enlarged wellbore diameter is greater than the pass-through diameter.

20. A method of real-time underreaming below a restriction in a well, comprising:
providing a drill-bit and an extendable tool to underream and increase a diameter of a borehole greater than a diameter of the drill-bit after passing through the restriction, said tool being activated to extend extendable blocks on the extendable tool to underream a diameter greater than that of the restriction and the drill-bit;
rotating said extendable tool and moving it axially along said borehole;
sensing a relative position of the extendable blocks to a body of the extendable tool using a position sensor;
measuring a borehole diameter using a caliper;
sensing a fluid property from one of a group comprising flow, rpm, weight, density, sound transit time and hydraulic force using at least one calibration sensor;
calibrating said measurements using a sensed fluid property from the at least one calibration sensor; and
using a processor, providing verification and control of a desired wellbore diameter by comparing and correlating data received from said caliper and from the position sensor to deliver the desired wellbore diameter.

21. The method of claim 20 wherein the cutter blocks position is compared and correlated with the measured underreamed wellbore diameter to achieve said desired wellbore diameter and reduce drilling downtime.

22. The method of claim 21, comprising using data received from the relative position of the extendable cutter blocks, from the caliper for measuring the underreamed wellbore diameter, and from the fluid properties sensor to a surface control area to transmit, data to a further location to achieve the desired wellbore diameter and reduce drilling time.

23. The method of claim 20, wherein the cutter block is activated using hydraulic force or fluid flow.

24. The method of claim 20, wherein the cutter block is lockable using hydraulic force or fluid flow.

25. The method of claim 20, further comprising:
at least one said cutter block movable within a tool body.

26. An underreaming apparatus comprising:
extendable blocks;
wellbore diameter measurement calipers to determine a wellbore diameter, the wellbore diameter measurement calipers incorporating fluid properties calibration sensors to calibrate said calipers, said extendable blocks and calipers housed in separate tool bodies connected to each other, the fluid properties calibration sensors sensing fluid properties from one of a group comprising flow, rpm, density, sound transit time, weight, and hydraulic force, the wellbore diameter measurement calipers using said fluid properties calibration sensors and at least one telemetry system located at longitudinally separated positions each connected to a tool body;
a position sensor to sense a relative position of the extendable block to a tool body:
a first housing to underream the wellbore;
a second housing to stabilize the underreaming tool within the walls of the wellbore during expansion;
a third housing to measure wellbore diameter;
a fourth housing to transmit data; and
at least one processor inter-connecting the wellbore diameter measurement calipers and the fluid properties calibration sensors, said processor providing verification and control of a desired wellbore diameter by comparing simultaneous measurements from the wellbore diameter measurement calipers and from the position sensor, and compensating the measurements using said fluid properties calibration sensors.

27. The underreaming apparatus according to claim 26, further comprising:
the extendable blocks and the wellbore diameter measurement calipers incorporating data from the fluid properties calibration sensors to calibrate the caliper with at least two expansion housings configured with the extendable cutter blocks, the wellbore diameter measurement calipers incorporating said fluid properties calibration and the at least one said telemetry system located at longitudinally separated positions.

28. A method of closed loop underreaming to provide a wellbore of a predetermined diameter, comprising:
a drilling rig in contact with a downhole processor, the downhole processor measuring an underreamed wellbore diameter using an acoustic caliper;
sensing a relative position of the extendable blocks to a body of the extendable tool using a position sensor;
sensing a fluid property from one of a group comprising flow, rpm, density, sound transit time, weight, and hydraulic force using at least one calibration sensor;
calibrating said acoustic caliper using a sensed fluid property from the at least one calibration sensor;
using a processor, providing verification and control of the predetermined diameter by comparing and correlating data received from said acoustic caliper and from the position sensor to deliver the predetermined diameter; and
comparing measured underreamed wellbore diameter with one or more of: calibration data, fluid properties, flow rate, underreamer cutter block position, weight and revolutions per minute to verify underreaming and delivery a desired wellbore diameter.

29. The method of claim 28 wherein a chamber is pressure compensated to the wellbore.

30. The method of claim 28 wherein a chamber is hydraulically sealed.

31. A method of closed loop underreaming to provide wellbore of a predetermined diameter, comprising:
providing a drilling rig in contact with a downhole processor, the downhole processor measuring underreamed wellbore diameter using an acoustic caliper;
sensing a relative position of the extendable blocks to a body of the extendable tool using a position sensor;
sensing a fluid property from one of a group comprising flow, rpm, density, sound transit time, weight, and hydraulic force using at least one calibration sensor;
calibrating said acoustic caliper using a sensed fluid property from the at least one calibration sensor;
using a processor, providing verification and control of the predetermined diameter by comparing and correlating data received from said acoustic caliper and from the position sensor to deliver the predetermined diameter; and
comparing a measured underreamed wellbore diameter with one or more of: acoustic calibration data, fluid properties, flow rate, underreamer cutter block position, weight and revolutions per minute to verify underreaming and delivery of the predetermined diameter.

32. A method of real time reaming, comprising:

providing a drill-bit and an extendable tool to ream a borehole;

passing through a restriction;

activating said tool to extend extendable cutter blocks to a diameter greater than the diameter of the drill-bit;

sensing a relative position of the extendable cutter blocks to a body of the tool using a position sensor;

rotating said tool and moving it axially along said borehole;

measuring a borehole diameter using at least one caliper;

sensing a fluid property from one of a group comprising flow, rpm, density, sound transit time, weight, and hydraulic force using at least one calibration sensor:

calibrating said caliper using a sensed fluid property from the calibration sensor; and using a processor connected to a control area which act in response to data received from said at least one caliper, verifying and controlling a predetermined diameter by comparing and correlating data received from the at least one caliper and from the position sensor to deliver the predetermined diameter.

\* \* \* \* \*